United States Patent [19]

Kim

[11] Patent Number: 5,094,836

[45] Date of Patent: Mar. 10, 1992

[54] MIXED HG-NI REAGENTS FOR SCREENING DIAGNOSIS OF CANCER

[75] Inventor: Yong J. Kim, Seoul, Rep. of Korea

[73] Assignee: Sam IL Pharmaceutical Manufacturing Co., Ltd., Rep. of Korea

[21] Appl. No.: 580,377

[22] Filed: Sep. 10, 1990

Related U.S. Application Data

[63] Continuation-in-part of Ser. No. 322,152, Mar. 10, 1989, abandoned.

[30] Foreign Application Priority Data

Mar. 11, 1988 [KR] Rep. of Korea ............... 2511/88

[51] Int. Cl.$^5$ .............. G01N 33/15; A61K 33/26; A61K 33/28; A61K 33/00
[52] U.S. Cl. .................... 424/7.1; 424/644; 424/646; 424/718; 514/908
[58] Field of Search .............. 424/7.1, 644, 718, 646; 514/908

[56] References Cited

U.S. PATENT DOCUMENTS 3,271,465 9/1966 Krewer et al. ............... 570/195

OTHER PUBLICATIONS

Kido y et al., "An Improved Method for the Millon Reaction" Chem. Pharm. Bull. 29(8):2296-2302 (1981).
Warren, K. S. et al., "Interfering Ultraviolet-Absorbing Compounds as Sources of Error in Common Clinical Chemistry Tests", Clinical Chemistry 15(12): 1147-1156 (1969).
Y. J. Kim et al., "Sensitivity and Specificity of the Reagent for Cancer Diagnosis Obtained by Urine NMR Measurement", *The New Medical Journal*, 28(2):51-54 (1985).
Yong J. Kim, "The Study of Possibility of Finding a Reagent for Cancer Diagnosis by Urine NMH Measurement", *J. of the Korea Society of Medical & Biological Engineering*, 7(1):35-39 (1986).
Manki Park et al., "Development of Reagent for Cancer Diagnosis by Urine Color Reaction (I)-Comparative Analysis of Cancer and Non-Cancer Urine by NMR, HPLC and Gift Reagent", *Arch. Pharm. Res.*, 11(2):134-138 (1988).
Yong-Jin Kim et al., "The Possible Reagents for a Cancer Diagnosis by a Urine Color Reaction", *Journal of the Korea Society of Medical and Biological Engineering*, 8(2):145-149 (1987).

Primary Examiner—Glennon H. Hollrah
Assistant Examiner—Gary E. Hollinden
Attorney, Agent, or Firm—Seed and Berry

[57] ABSTRACT

There is disclosed a composition and method for detecting the presence of cancer in humans. The method includes contacting a sample of human urine with a composition which reacts with the urine to form a colored precipitate to indicate the presence of cancer. The composition includes mercury, nickel, nitric acid and distilled water, and may further be admixed with a material to form a gel.

4 Claims, No Drawings 5,094,836

MIXED HG-NI REAGENTS FOR SCREENING DIAGNOSIS OF CANCER

RELATED APPLICATION

This application is a continuation-in-part of U.S. Ser. No. 322,152, filed Mar. 10, 1989, now abandoned.

TECHNICAL FIELD

The present invention relates generally to the detection of cancer and, more specifically, to a mixed mercury-nickel (Hg-Ni) composition for use in screening patients for the presence of cancer.

BACKGROUND OF THE INVENTION

An increasing interest in cancer diagnosis has led to an attempt to find reagents useful in the diagnosis of cancer by their reaction with components of urine to produce a colored precipitate. Since a variety of metabolites are excreted in human urine, it has been suggested that the amount of specific metabolites in a patient's urine will vary depending upon the disease state of the patient. It has been found that the distribution of nuclear magnetic resonance (NMR) signals of the urine of cancer patients are quite different from those of the urine of noncancer patients. Specifically, NMR signals in the range of 3.00 ppm to 3.09 ppm are commonly observed in the urine of cancer patients.

As disclosed in Korean Patent No. 21558, the specific NMR signals observed in the urine of cancer patients are related to the presence of phenolic metabolites, such as tyrosine. Korean Patent No. 21558 also discloses a reagent (i.e., Millon's reagent) for use as a cancer diagnosis agent which identifies the presence of tyrosine in urine by the formation of a colored precipitate.

However, the use of Millon's reagent in the urine test is highly disadvantageous because of the instability of the precipitate formed in the reaction. The reason for this instability is that the mercury ions in Millon's reagent have a high complex-forming capacity but a relatively low ionization tendency in comparison with other metal ions. Thus, it is easily interfered with by inorganic salts and aromatic organocompounds that are coexisting in the urine sample.

Accordingly, there is a need in the art for reagents which react with the specific components present in the urine of cancer patients, and which do not exhibit the disadvantages, such as instability of the colored precipitate, associated with Millon's reagent.

SUMMARY OF THE INVENTION

The present invention discloses a method for detecting cancer in humans by contacting a sample of human urine with a mixed Hg-Ni composition which reacts with the urine to form a colored precipitate to indicate the presence of cancer. The present invention also discloses a composition for use in the above method. The composition comprises mercury, nickel, nitric acid and distilled water, wherein the nickel is present at a concentration ranging from about 0.1 to about 0.3 parts by weight to 1 part by weight mercury, wherein the nitric acid is about 9 M and is present in an amount ranging from about 2 ml to about 5 ml of nitric acid to 1 gram mercury, and wherein distilled water is present in an amount substantially equal to the volume of nitric acid. The composition may also be admixed with a material to form a gel.

DETAILED DESCRIPTION OF THE INVENTION

The present invention relates to a mixed mercury-nickel (Hg-Ni) composition which can be used in screening for the presence of cancer through a color reaction by identifying the phenolic metabolites which exist in greater quantities in cancer patients than in persons without cancer.

Millon's reagent is a nitric acid solution of mercury. In order to compensate for the disadvantageous properties of mercury, tyrosine was reacted with other metallic ions in place of the mercury ions, based on the fact that the reaction between Millon's reagent and tyrosine is primarily due to the formation of a complex with said mercury ions. As a result, it was confirmed that tyrosine also reacts with nitric acid solutions of either cadmium (Cd), zinc (Zn), copper (Cu) or nickle (Ni) to form a red complex compound.

However, when the nitric acid solutions of these metals are applied to the urine samples of cancer patients in place of Millon's reagent, no reaction is observed. It is postulated that the reasons for this are that: (1) the complex-forming capacity of these metal ions is relatively low when compared to that of the mercury ion, and (2) the content of aromatic amines present in the urine of the cancer patients is so small that it does not reach the concentration level capable of initiating the reaction with these alternative metal ions.

These metals have a low complex-forming capacity, and a high ionization tendency. Accordingly, it is proposed that these metals may function as either a substitute for mercury in the mercury complexes or as a cross-linking agent between the complexes to stabilize the complexes. On the basis if this, Millon's reagent was combined with each of the above-mentioned metals and it was found that the combination of Millon's reagent with nickel gave a more stable precipitate than that of Millon's reagent alone. That is, when Millon's reagent is used alone, the complex obtained is unstable and dissolved easily, depending on the condition of the sample, and therefore, the reading of the results is difficult.

However, the mixed Hg-Ni composition of the present invention does not produce such an undesired phenomenon and the reading of the reaction results is simplified because the color of the reaction precipitate is stable and persists for a longer period of time.

The mixed Hg-Ni composition of the present invention includes mercury, nickel, nitric acid, and distilled water. Preferably, the amount of nickel needed for maintaining the stable color of the precipitate during the reading period is 0.1 to 0.3 parts by weight of nickel per one part by weight of mercury. If the mixing ratio between mercury and nickel contains too much mercury, the precipitate obtained is unstable. If the ratio is higher in nickel, the amount of the precipitate is reduced bringing about a poor diagnostic effect. Therefore, it is necessary to maintain a suitable mixing ratio.

The nitric acid included in the mixed Hg-Ni composition is preferably 9 molar and used at a ratio of 2 to 5 ml of nitric acid per gram of mercury. Distilled water is used in a substantially similar amount by volume to the nitric acid. However, if distilled water is used in excess, the amount of the precipitate is reduced, while too small an amount of distilled water will result in an unstable precipitate.

When 0.04 ml of the mixed Hg-Ni composition is added to 1 ml of a urine sample, a red precipitate is observed in the urine of cancer patients, while a white precipitate is observed in the urine of normally healthy persons.

In addition, the mixed Hg-Ni composition of the present invention can be applied to a screening test which is used to conveniently and rapidly detect for the presence of tyrosine amines in a large number of urine specimens. If the mixed Hg-Ni composition is mixed with agar to form a jelly phase, it becomes a suitable formulation for treatment, storage and transport. The jelly phase may be prepared by adding 3 to 5 g of agar in 100 ml of distilled water and heating to form a solution. The agar used therein should be better than the lower limit of the Korean Pharmacopoeia standard in purity. The mixed Hg-Ni composition is then added to the agar solution. Preferably, the mixed Hg-Ni composition is combined with the agar solution in a ratio of 1:10 by volume. After mixing, the resulting mixture is divided into test tubes of 1 cm diameter and filled to approximately 2 cm in height, followed by cooling at room temperature.

After about 5 ml of the urine specimen is added to each tube in which the jelly phase was formed, it remains standing for about five minutes in order to produce the precipitate between the layers of the mixture and the urine specimen.

If the precipitates are white or red, these can be read to be negative or positive, respectively. The advantage of the jelly phase is to reduce the hazardous conditions posed by the solution form of the mixed Hg-Ni composition. Thus, hazard to the experimenter may be decreased by having the nitric acid in a jelly phase rather than solution. On the other hand, the reactive sensitivity of the jelly is apt to decline somewhat compared to that of the solution.

The following examples are offered by way of illustration and not by way of limitation.

EXAMPLE 1

10 ml of a solution of 50 g of metallic mercury dissolved in 50 ml of 9 M nitric acid is mixed with 20 ml of a solution of 5 g of metallic nickel dissolved in 50 ml of nitric acid, and the resulting solution is then diluted with the addition of 30 ml of distilled water.

EXAMPLE 2

Using a glass stirrer, 5 g of agar is dissolved in 10 ml of distilled water in a 300 ml beaker with heat prior to sufficiently mixing with 10ml of the reagent solution prepared in Example 1 The mixed solution is poured into a glass tube of 1 cm diameter and is filled to 2 cm high, and is then solidified by cooling at room temperature.

EXAMPLE 3

The mixed Hg-Ni compositions prepared in Examples 1 and 2 above were tested in the following assay:

Three ml of a subject's urine is taken up prior to adding 0.15 ml of the mixed Hg-Ni composition solution prepared in Example A red-colored precipitate formed therefrom is judged as being positive and the white-colored precipitate formed is judged as being negative.

Alternatively, when the jelly phase test method is employed, 5 ml of the subject's urine is added to the mixed Hg-Ni composition jelly prepared in Example 2. After waiting five minutes, a red or a white band of precipitate is formed at the boundary between the jelly and urine phases and is judged as being positive or negative, respectively.

Urine samples obtained from 34 patients who were judged as suffering from cancer by a histological assay and urine samples from 35 non-cancer patients were tested in the manner described above. The test results for all 69 patients are given in Table 1.

The test confirmed the presence of cancer which was previously detected under histological examination. Thus, the clinical value of the mixed Hg-Ni composition of the present invention is that it can be utilized to aid in the diagnosis of cancer. In this way, large populations can be screened for the potential presence of cancer, prior to employing close examination.

It is emphasized that cancer should be detected early so that treatment can be initiated at an early stage to obtain better success rates. Accordingly, the screening method for the diagnosis of cancer using the mixed Hg-Ni composition of the present invention is useful for early detection of cancer.

TABLE 1

The results of mixed Hg-Ni salt solution and jellied form in cancer and non-cancer patients

| No. | age | sex | diagnosis | type | Results solution | jelly form |
|---|---|---|---|---|---|---|
| 1 | 43 | F | breast ca | Malignant | + | + |
| 2 | 49 | M | laryngeal ca | Malignant | + | + |
| 3 | 50 | M | stomach | Malignant | + | + |
| 4 | 63 | F | lung squam ca | Malignant | + | + |
| 5 | 47 | M | lectal ca | Malignant | + | + |
| 6 | 57 | M | transi, cell ca | Malignant | + | + |
| 7 | 63 | M | hepatocell ca | Malignant | + | − |
| 8 | 69 | M | stomach ca | Malignant | + | + |
| 9 | 69 | F | esophageal ca | Malignant | + | + |
| 10 | 51 | M | stomach ca | Malignant | + | + |
| 11 | 53 | F | rectal ca | Malignant | + | + |
| 12 | 46 | M | lung ca | Malignant | + | − |
| 13 | 45 | M | laryngeal ca | Malignant | + | + |
| 14 | 60 | M | GB ca | Malignant | + | + |
| 15 | 64 | M | stomach ca | Malignant | − | − |
| 16 | 17 | F | ALL | Malignant | + | + |
| 17 | 64 | F | bronchogenic ca | Malignant | − | − |
| 18 | 59 | M | hepatocell ca | Malignant | + | + |
| 19 | 48 | M | stomach ca | Malignant | + | + |
| 20 | 49 | M | periampul ca | Malignant | + | + |
| 21 | 36 | F | cervical ca | Malignant | + | − |
| 22 | 62 | M | stinacg ca | Malignant | + | + |
| 23 | 63 | M | bronchogenic ca | Malignant | + | + |
| 24 | 13 | M | ALL | Malignant | + | + |
| 25 | 67 | M | colon ca | Malignant | + | + |
| 26 | 79 | M | bronchogenic ca | Malignant | + | + |
| 27 | 70 | F | lung ca | Malignant | + | + |
| 28 | 80 | F | stomach ca | Malignant | − | − |
| 29 | 32 | M | stomach ca | Malignant | + | + |
| 30 | 57 | M | stomach ca | Malignant | + | + |
| 31 | 50 | F | mullerian ca | Malignant | + | + |
| 32 | 64 | M | stomach ca | Malignant | + | + |
| 33 | 70 | M | stomach ca | Malignant | − | − |
| 34 | 35 | F | Inv. ductal ca | Malignant | − | − |
| 35 | 72 | M | leiomyosarcoma | Benign | − | − |
| 36 | 61 | M | pneumonia | Normal | − | − |
| 37 | 48 | F | GB stone | Normal | − | − |
| 38 | 36 | M | DM | Normal | − | − |
| 39 | 44 | M | pyelonephritis | Normal | − | − |
| 40 | 30 | M | TB, RA, sjogren | Normal | + | + |
| 41 | 18 | M | enchondroma | Benign | − | − |
| 42 | 21 | M | pleurisy TD | Normal | − | − |
| 43 | 29 | F | pregnancy | Normal | − | − |
| 44 | 53 | F | hashimoto | Normal | − | − |
| 45 | 39 | F | uelomyoma | Benign | + | − |
| 46 | 54 | F | unknown, CYTO | Normal | − | − |
| 47 | 42 | M | pleurisy, TB | Normal | − | − |
| 48 | 64 | M | appendicitis | Normal | − | − |
| 49 | 53 | F | insert. obstuct | Normal | − | − |
| 50 | 16 | F | bronchial cleft | Normal | − | − |
| 51 | 6 | F | lipomatosis | Normal | − | − |

TABLE 1-continued

The results of mixed Hg-Ni salt solution and jellied form in cancer and non-cancer patients

| No. | age | sex | diagnosis | type | Results solution | jelly form |
|---|---|---|---|---|---|---|
| 52 | 65 | M | CHR gastritis | Normal | − | − |
| 53 | 61 | F | CHR bronchitis | Normal | − | − |
| 54 | 64 | F | renal cyst | Normal | + | + |
| 55 | 26 | F | nonsp colitis | Normal | − | − |
| 56 | 37 | F | placenta previa | Normal | − | − |
| 57 | 36 | F | leimyoma | Benign | − | − |
| 58 | 55 | M | pleural TB | Normal | − | − |
| 59 | 70 | M | CHR PN | Normal | − | − |
| 60 | 43 | F | adenomyosis | Normal | − | − |
| 61 | 37 | M | bronchiectasis | Normal | − | − |
| 62 | 26 | M | anal fistula | Normal | − | − |
| 63 | 74 | M | hemoptysis | Normal | − | − |
| 64 | 38 | F | hydroureter | Normal | − | − |
| 65 | 55 | M | gastritis | Normal | − | − |
| 66 | 67 | F | GB stone | Normal | − | − |
| 67 | 24 | M | pleura TB | Normal | − | − |
| 68 | 28 | F | L/N TB | Normal | − | − |
| 69 | 62 | F | acute cytosis | Normal | − | − |

The detection sensitivity, detection specificity, false positive rate, false negative rate, positive predictive value and negative predictive value are summarized in Table 2 utilizing the following calculations:

$$\text{Detection sensitivity} = \frac{\text{persons determined as positive by test}}{\text{total cancer patients in test}}$$

$$\text{Detection specificity} = \frac{\text{persons determined as negative by test}}{\text{total non-cancer patients in test}}$$

$$\text{False positive rate} = \frac{\text{persons determined as positive by test}}{\text{total non-cancer patients in test}}$$

$$\text{False negative rate} = \frac{\text{persons determined as negative by test}}{\text{total cancer patients in test}}$$

Positive predictive value =

$$\frac{\text{real cancer patients determined as positive}}{\text{total persons determined as positive by test}}$$

Negative predictive value =

$$\frac{\text{real non-cancer patients determined as negative by test}}{\text{total persons determined as negative by test}}$$

TABLE 2

|  | Solution | Jelly Form |
|---|---|---|
| Detection sensitivity | 78.4% | 76.5% |
| Detection specificity | 91.4% | 94.3% |
| False positive rate | 8.6% | 5.7% |
| False negative rate | 21.6% | 23.5% |
| Positive predictive value | 90.6% | 92.9% |
| Negative predictive value | 86.5% | 80.5% |

From the foregoing it will be appreciated that, although specific embodiments of the invention have been described herein for purposes of illustration, various modifications may be made without deviating from the spirit and the scope of the invention. Accordingly, the invention is not to be limited except as by the appended claims.

I claim:

1. A composition comprising mercury, nickel, nitric acid and distilled water, wherein nickel is present at a concentration ranging from about 0.1 to about 0.3 parts by weight nickel to one part by weight mercury, wherein the nitric acid is about 9 molar and is present in an amount ranging from about 2 ml to about 5 ml of nitric acid to 1 gram mercury, and wherein water is present in an amount substantially equal to the volume of nitric acid.

2. The composition of claim i wherein said composition is admixed with a material to form a gel.

3. A method for detecting cancer in a human comprising contacting a sample of urine taken from the human with a composition which reacts with the urine to form a colored precipitate to indicate the presence of cancer in the human, said composition comprising mercury, nickel, nitric acid and distilled water, wherein nickel is present at a concentration ranging from about 0.1 to about 0.3 parts by weight nickel to one part by weight mercury, wherein the nitric acid is about 9 molar and is present in an amount ranging from about 2 ml to about 5 ml of nitric acid to 1 gram mercury, and wherein water is present in an amount substantially equal to the volume of nitric acid.

4. The method of claim 3 wherein said composition is admixed with a material to form a gel.

* * * * *

UNITED STATES PATENT AND TRADEMARK OFFICE
CERTIFICATE OF CORRECTION

PATENT NO. : 5,094,836
DATED : March 10, 1992
INVENTOR(S) : Yong J. Kim

It is certified that error appears in the above-identified patent and that said Letters Patent is hereby corrected as shown below:

In column 6, claim 2, line 31, please delete "claim i" and substitute therefor -- claim 1 --.

Signed and Sealed this

First Day of June, 1993

Attest:

MICHAEL K. KIRK

*Attesting Officer*   Acting Commissioner of Patents and Trademarks